United States Patent
Ishida et al.

(10) Patent No.: US 12,062,796 B2
(45) Date of Patent: Aug. 13, 2024

(54) CORE-SHELL CATALYST FOR OXYGEN REDUCTION REACTION, AND METHOD OF DESIGNING CATALYST

(71) Applicants: TANAKA KIKINZOKU KOGYO K.K., Tokyo (JP); NATIONAL INSTITUTE OF TECHNOLOGY, Hachioji (JP)

(72) Inventors: Minoru Ishida, Hiratsuka (JP); Koichi Matsutani, Hiratsuka (JP); Hiroshi Nakanishi, Akashi (JP); Hideaki Kasai, Akashi (JP); Bhume Chantaramolee, Akashi (JP); Susan Menez Aspera, Akashi (JP)

(73) Assignees: TANAKA KIKINZOKU KOGYO K.K., Tokyo (JP); NATIONAL INSTITUTE OF TECHNOLOGY, Hachioji (JP)

( * ) Notice: Subject to any disclaimer, the term of this patent is extended or adjusted under 35 U.S.C. 154(b) by 0 days.

(21) Appl. No.: 18/268,899

(22) PCT Filed: Dec. 13, 2021

(86) PCT No.: PCT/JP2021/045775
§ 371 (c)(1),
(2) Date: Jun. 21, 2023

(87) PCT Pub. No.: WO2022/138270
PCT Pub. Date: Jun. 30, 2022

(65) Prior Publication Data
US 2023/0395818 A1    Dec. 7, 2023

(30) Foreign Application Priority Data
Dec. 22, 2020   (JP) ................................. 2020-212227

(51) Int. Cl.
| | | |
|---|---|---|
| H01M 4/92 | (2006.01) | |
| H01M 8/10 | (2016.01) | |
| H01M 8/1018 | (2016.01) | |

(52) U.S. Cl.
CPC ........... *H01M 4/921* (2013.01); *H01M 4/926* (2013.01); *H01M 8/1018* (2013.01); *H01M 2008/1095* (2013.01)

(58) Field of Classification Search
CPC .... H01M 4/921; H01M 4/926; H01M 8/1018; H01M 2008/1095; H01M 4/86;
(Continued)

(56) References Cited

U.S. PATENT DOCUMENTS

| | | |
|---|---|---|
| 2012/0005888 A1 | 1/2012 | Nakai et al. |
| 2012/0046164 A1* | 2/2012 | Tanaka ................. B01J 37/0211 502/305 |

(Continued)

FOREIGN PATENT DOCUMENTS

| | | |
|---|---|---|
| CN | 102822389 A | 12/2012 |
| JP | 5152942 B1 | 1/2014 |

(Continued)

OTHER PUBLICATIONS

International Searching Authority, "International Search Report," issued in connection with International Patent Application No. PCT/JP2021/045775, dated Feb. 15, 2022.

(Continued)

*Primary Examiner* — Daniel S Gatewood
(74) *Attorney, Agent, or Firm* — Foley & Lardner LLP (57) ABSTRACT

A catalyst for an oxygen reduction reaction containing catalyst particles having a shell-core structure containing a PtCo alloy or a PtCoMn alloy as a core, and platinum as a shell layer. A specific plane of a face-centered cubic lattice is formed by a plurality of platinum atoms contained in the (Continued)

shell layer, and a lattice constant of the plane of the face-centered cubic lattice on the catalyst particle surface is 3.70 Å or more and 4.05 Å or less (in a PtCo alloy), or 3.870 Å or more and 4.10 Å or less (in a PtCoMn alloy). A catalyst design method includes a step of calculating, with respect to an orientation plane such as the plane formed by platinum atoms of the shell layer, adsorption energies for an oxygen molecule, an OH group and a water molecule by first-principles calculation based on density functional theory.

13 Claims, 8 Drawing Sheets

(58) Field of Classification Search
CPC ........ H01M 4/9083; H01M 4/92; H01M 8/10; Y02E 60/50; Y02P 70/50
See application file for complete search history.

(56) References Cited

U.S. PATENT DOCUMENTS

| | | | |
|---|---|---|---|
| 2014/0200133 A1 | 7/2014 | Kimura et al. | |
| 2015/0125783 A1 | 5/2015 | Ishida et al. | |
| 2015/0249252 A1* | 9/2015 | Abruna .................. | H01M 4/926 429/535 |
| 2015/0372314 A1 | 12/2015 | Ishida et al. | |
| 2018/0138518 A1 | 5/2018 | Matsutani et al. | |
| 2020/0122123 A1 | 4/2020 | Matsutani et al. | |

FOREIGN PATENT DOCUMENTS

| | | |
|---|---|---|
| JP | 5531125 B1 | 6/2014 |
| JP | 2016-043314 A | 4/2016 |
| KR | 2020-0053431 A | 5/2020 |
| TW | 201706037 A | 2/2017 |
| WO | WO-2006/045606 A1 | 5/2006 |
| WO | WO-2011/125197 A1 | 10/2011 |
| WO | WO-2017/010233 A1 | 1/2017 |
| WO | WO-2018/131206 A1 | 7/2018 |

OTHER PUBLICATIONS

International Searching Authority, "Written Opinion," issued in connection with International Patent Application No. PCT/JP2021/045775, dated Feb. 15, 2022.

Japanese Patent Office, "Notice of Reasons for Refusal," issued in connection with Japanese Patent Application No. 2020-212227, dated Feb. 14, 2022.

Taiwanese Patent Office, "Office Action," issued in connection with Taiwanese Patent Application No. 110146956, dated Aug. 29, 2022.

* cited by examiner

Fig. 1 (a) OXYGEN MOLECULE DISSOCIATION

Fig. 1 (b) PEROXY DISSOCIATION

Fig. 1 (c) HYDROGEN PEROXIDE DISSOCIATION

CORE-SHELL CATALYST FOR OXYGEN REDUCTION REACTION, AND METHOD OF DESIGNING CATALYST

CROSS-REFERENCE TO RELATED APPLICATIONS

The present application claims priority under 35 U.S.C. § 371 to International Patent Application No. PCT/JP2021/045775, filed Dec. 13, 2021, which claims priority to and the benefit of Japanese Patent Application No. 2020-212227, filed on Dec. 22, 2020. The contents of these applications are hereby incorporated by reference in their entireties.

BACKGROUND OF THE INVENTION

Field of the Invention

The present invention relates to a catalyst for promoting an oxygen reduction reaction occurring in a cathode reaction or the like of a fuel cell. It also relates to a method for designing a catalyst for an oxygen reduction reaction utilizing density functional theory.

Description of the Related Art

As a catalyst for accelerating an oxygen reduction reaction (ORR) occurring in a cathode of a fuel cell, a Pt catalyst using Pt (platinum) as a catalyst particle is conventionally known. A Pt catalyst is highly active in ORR, and hence has been useful as a cathode catalyst since the early stage of development of fuel cells.

On the other hand, considering that platinum is a rare and expensive precious metal, attempts have been made to reduce the amount of platinum used in a catalyst. The present applicant also has disclosed a large number of examination examples on a catalyst using, as a catalyst particle, an alloy of platinum and another metal (Pt alloy). Examples of a Pt alloy catalyst proposed by the present applicant include a PtCo catalyst using an alloy of platinum and cobalt as a catalyst particle, and a PtCoMn catalyst using an alloy of platinum, cobalt, and manganese as a catalyst particle. It has been revealed that these Pt alloy catalysts can exhibit activity equivalent to or higher than that of a Pt catalyst although the amount of platinum used is reduced.

In addition, for improvement of a Pt alloy catalyst, an approach from a structure of a catalyst particle is also known in addition to selection of metal species to be used in the alloy. In particular, it is known that a core-shell structure in which a core particle containing a metal except for platinum is covered with a shell layer of platinum can reduce the amount of platinum used as a whole with ensuring activity on the catalyst particle surface.

PRIOR ART DOCUMENT

Patent Document

Patent Document 1: Japanese Patent No. 5531125
Patent Document 2: Japanese Patent No. 5152942
Patent Document 3: International Publication No. WO2018/131206

SUMMARY OF THE INVENTION

Technical Problem

Owing to the improvement made in the composition and the structure of a catalyst particle described above, it is considered that conventional Pt alloy catalysts have achieved suppressing the amount of platinum used, and this problem has been solved more or less. Under this circumstance, it seems that improvement in catalytic activity will be more strongly demanded. Not only in application to an oxygen reduction reaction but also in development of catalysts, improvement of activity is a priority issue. In this respect, the Pt alloy catalysts (the PtCo catalyst and the PtCoMn catalyst) of the present applicant have activity equivalent to or higher than that of a Pt catalyst, but there still is room for improvement.

Further, in conventional catalyst design, it is difficult to predict whether or not activity in a target reaction can be obtained depending on selection of a metal to be added to platinum and a catalyst preparation method. It is essential to perform experimental verification for discovering a structure of a useful catalyst, but it is not easy to perform experimental verification on innumerable structures of catalysts.

The present invention has been achieved under these circumstances, and an object is to provide a Pt alloy catalyst for an oxygen reduction reaction in a cathode of a fuel cell or the like that is more excellent in activity than a Pt catalyst. In addition, as a method for designing a catalyst for an oxygen reduction reaction, a catalyst design method capable of estimating a preferred catalyst structure prior to experimental verification will be clarified.

Solution to Problem

The present invention for solving the above-described problem provides a catalyst for an oxygen reduction reaction, containing a catalyst particle having a core-shell structure containing a PtCo alloy as a core, and platinum as a shell layer, wherein a plurality of platinum atoms contained in the shell layer form a (111) plane of a face-centered cubic lattice, and a lattice constant of the (111) plane of the face-centered cubic lattice on a surface of the catalyst particle is 3.70 Å or more and 4.05 Å or less.

In the catalyst of the present invention, a lattice constant of a (111) plane of the face-centered cubic lattice formed by platinum atoms present inside the catalyst particle is smaller than a lattice constant of a (111) plane of the face-centered cubic lattice on a surface of the catalyst particle. Specifically, a lattice constant of a (111) plane of the face-centered cubic lattice formed by platinum atoms present inside the catalyst particle is 3.55 Å or more and 3.95 Å or less.

In the catalyst, the PtCo alloy contained in the core can be represented by $PtCo_x$ (wherein $0.14 \leq x \leq 0.33$).

Alternatively, the present invention provides a catalyst for an oxygen reduction reaction, containing a core-shell structure containing a PtCoMn alloy as a core, and platinum as a shell layer, wherein a plurality of platinum atoms contained in the shell layer form a (111) plane of a face-centered cubic lattice, and a lattice constant of the (111) plane of the face-centered cubic lattice on a surface of the catalyst particle is 3.870 Å or more and 4.10 Å or less.

In the catalyst of the present invention, a lattice constant of a (111) plane of the face-centered cubic lattice formed by platinum atoms present inside the catalyst particle is smaller than a lattice constant of a (111) plane of the face-centered cubic lattice on the surface of the catalyst particle. Specifically, a lattice constant of a (111) plane of the face-centered cubic lattice formed by platinum atoms present inside the catalyst particle is 3.70 Å or more and 4.05 Å or less.

In the catalyst, the PtCoMn alloy contained in the core can be represented by $PtCo_yMn_z$ (wherein $0.06 \leq y \leq 0.39$, and $0.04 \leq z \leq 0.33$).

In the catalyst of the present invention, an absolute value of an adsorption energy in an adsorption site having a maximum oxygen atom adsorption energy is less than 1.0 eV. Alternatively, in the catalyst, an absolute value of an adsorption energy in an adsorption site having a maximum oxygen molecule adsorption energy is less than 0.5 eV. In the catalyst of the present invention, an absolute value of an adsorption energy in an adsorption site having a maximum OH group adsorption energy is less than 2.3 eV. In the catalyst of the present invention, an absolute value of an adsorption energy in an adsorption site having a maximum water molecule adsorption energy is less than 0.19 eV.

The catalyst of the present invention can be constituted by supporting the catalyst particle on a carbon fine powder carrier used as a carrier. A supporting density of the catalyst particle in the entire catalyst in this case is preferably 20 to 70% by mass.

The present application provides a method for designing a catalyst for an oxygen reduction reaction, the catalyst containing a catalyst particle having a core-shell structure containing, as a core, an alloy consisting of platinum and one or more alloy elements, and platinum as a shell layer, the method including: a step of selecting at least any one of orientation planes of a (111) plane, a (001) plane, and a (110) plane as arrangement of a plurality of platinum atoms contained in the shell layer; a step of creating an adsorption model for an oxygen molecule, an OH group generation model, and a water molecule generation and desorption model with respect to the selected orientation plane of platinum; and a step of calculating an adsorption energy for the oxygen molecule, an OH group adsorption energy, and a water molecule adsorption energy by first-principles calculation based on density functional theory, wherein the alloy elements are selected based on calculation results of the adsorption energy, the OH group adsorption energy, and the water molecule adsorption energy.

Advantageous Effects of Invention

As described above, a catalyst for an oxygen reduction reaction of the present invention is a core-shell catalyst containing a specific Pt alloy as a core, and a shell layer containing platinum formed thereon. The core-shell catalyst of the present invention has more preferred activity than a Pt catalyst with reducing an amount of platinum used. In addition, according to a method for designing a catalyst for an oxygen reduction reaction of the present invention, density functional theory is utilized, so that a composition or structure of a catalyst particle having good activity can be estimated without performing experimental verification to design a catalyst.

DETAILED DESCRIPTION OF THE PREFERRED EMBODIMENTS (A) Core-Shell Catalyst of Invention A preferred embodiment of the present invention will now be described. As described above, a catalyst for an oxygen reduction reaction of the present invention has a core-shell structure using platinum as a shell layer, and a PtCo alloy or a PtCoMn alloy is applied as a core. These Pt alloys are used as the core because a conventional Pt alloy catalyst described above has preferred activity in ORR. Although the reason why the PtCo alloy and the PtCoMn alloy have good activity has not been completely cleared, the present inventors presume that core-shell catalysts using these as the core can be also expected to exhibit high activity.

In these Pt alloys contained in the core of the core-shell catalyst, the PtCo alloy is preferably $PtCo_x$ ($0.14 \leq x \leq 0.33$), and the PtCoMn alloy is preferably $PtCo_yMn_z$ ($0.06 \leq y \leq 0.39$, and $0.04 \leq z \leq 0.33$). It is noted that a core-shell catalyst herein is expressed in the order of a shell/a core. A catalyst containing the PtCo alloy as a core and a Pt shell layer formed thereon is expressed as a Pt/PtCo catalyst, and a catalyst containing the PtCoMn alloy as a core and a Pt shell layer formed thereon is expressed as a Pt/PtCoMn catalyst. Besides, a Pt/PtCo catalyst and a Pt/PtCoMn catalyst encompass those using, as the core, the PtCo alloy and the PtCoMn alloy having the above-described compositions ($PtCo_x$ and $PtCo_yMn_z$).

The present invention employs the core-shell structure for the catalyst mainly for purposes of reducing the amount of platinum used in the catalyst. It is, however, considered, in addition to the reduction of the amount of platinum used, that activity in ORR is improved as compared with that of a Pt catalyst by using platinum atoms in an appropriate state as a shell layer. For purposes of improving the activity in the present invention, a plurality of platinum atoms contained in the shell layer form the (111) plane of a face-centered cubic lattice.

In the PtCo catalyst, the (111) plane of a face-centered cubic lattice on the surface of the catalyst particle has a lattice constant of 3.70 Å or more and 4.05 Å or less. At this point, it is preferable that the lattice constant of the (111) plane of the face-centered cubic lattice formed by platinum atoms present inside the catalyst particle is smaller than the lattice constant of the (111) plane of the face-centered cubic lattice on the catalyst particle surface. Specifically, the lattice constant of the (111) plane of the face-centered cubic lattice formed by platinum atoms present inside the catalyst particle is preferably 3.55 Å or more and 3.95 Å or less.

On the other hand, in the PtCoMn catalyst, the (111) plane of a face-centered cubic lattice on the catalyst particle surface has a lattice constant of 3.870 Å or more and 4.10 Å or less. At this point, it is preferable that the lattice constant of the (111) plane of a face-centered cubic lattice formed with platinum atoms present inside the catalyst particle is smaller than the lattice constant of the (111) plane of a face-centered cubic lattice on the catalyst particle surface. Specifically, the lattice constant of the (111) plane of the face-centered cubic lattice formed by platinum atoms present inside the catalyst particle is preferably 3.70 Å or more and 4.05 Å or less.

It is noted that the number of layers of platinum atoms in the shell layer is preferably 1 atomic layer (monoatomic layer) or more and 3 atomic layers or less.

Arrangement of platinum atoms in the shell layer can be checked by high-angle annular dark-field scanning transmission electron microscopy STEM (HAADF-STEM) or spherical aberration corrected scanning transmission electron microscopy (cs-STEM). In particular, cs-STEM is useful in structural analysis of a cross-section of a catalyst particle. Besides, the lattice constant of a prescribed crystal plane can be calculated based on a measurement result of lattice spacing obtained by cs-STEM. Alternatively, the measurement can be performed by using X-ray absorption fine structure (XAFS) or extended X-ray absorption fine structure (EXAFS).

The core-shell catalyst of the present invention is preferably in a form a supported catalyst supported on an appropriate carrier. The carrier is a substrate used in a process of forming a core-shell catalyst particle, and corresponds to a carrier in use process. In application to a fuel cell, it also acts as a conductive material of a cathode electrode. The carrier is preferably a carbon fine powder, and a carbon fine powder having an appropriate pore is preferably used. The carbon fine powder has a specific surface area of preferably 50 to 1500 m$^2$/g.

An average particle size of the core-shell catalyst of the present invention is preferably 2 to 20 nm on average. In a coarse catalyst having a particle size over 20 nm, the activity is liable to lower, and when the particle size is less than 2 nm, a long-term activity keeping property cannot be definitely obtained, and therefore, the average particle size of the core-shell catalyst is more preferably 5 nm or less. The particle size of the core-shell catalyst refers to a particle size of the entire particle including the shell layer. The particle size can be estimated by XRD analysis, and on the basis of a full-width at half maximum of a peak of the Pt alloy in an XRD profile, the particle size can be calculated in accordance with Scherrer formula ($R=0.9\lambda/W\cos\theta$ (wherein R is a particle size (nm), $\lambda$ is a wavelength of X-ray (for example, CuK$\alpha$ ray has a wavelength of 0.154 nm), W is a full-width at half maximum (degree), and $\theta$ is an incident angle (degree)).

When the core-shell catalyst of the present invention is in the form of a supported catalyst, a supporting ratio of the catalyst is preferably 20 to 70%. The term "supporting ratio" refers to a ratio of the mass of the core-shell catalyst particle to the mass of the entire catalyst including the carrier.

As a method for producing the core-shell catalyst of the present invention, a method for producing a conventional core-shell catalyst can be applied as basic procedures. As the method for producing a core-shell catalyst, electrochemical methods such as under-potential deposition (UPD) and chemical methods such as liquid phase reduction are known. In the present invention, liquid phase reduction is preferably employed (Patent Document 1). In the production of a core-shell catalyst employing liquid phase reduction, metal salts of constituting elements of a Pt alloy used as a core (such as platinum, cobalt, and manganese) are supported on a carrier, and the resultant is subjected to heat treatment for forming the Pt alloy. Then, a particle of the thus formed Pt alloy is subjected to a treatment for forming a shell layer.

In supporting the metal salts of platinum, cobalt and manganese, the carrier of a carbon fine powder or the like is simultaneously impregnated with solutions of the metal salts. Alternatively, a Pt catalyst containing platinum alone supported on a carrier may be impregnated with the metal salts of cobalt and manganese (metal salt solutions). In this case, a commercially available Pt catalyst may be used. Preferably, the Pt catalyst of the latter case precedently produced/prepared is impregnated with the metal salts of cobalt and manganese (metal salt solutions). As the solutions of the metal salts, aqueous solutions of known metal salts (dinitrodiammineplatinum nitrate, chloroplatinate, potassium chloroplatinate, hexaammineplatinum hydroxide and the like for platinum, cobalt chloride hexahydrate, cobalt nitrate, cobalt acetate tetrahydrate and the like for cobalt, and manganese chloride tetrahydrate, magnesium nitrate hexahydrate, magnesium acetate tetrahydrate and the like for manganese) are preferably used. Then, the carrier impregnated with these metal salts (or the Pt catalyst) is subjected to a reduction treatment through contact with a reducing agent (such as an alcohol or sodium borohydride), and thus the metals are supported. The heat treatment for generating a Pt alloy after supporting the constituting elements of the core-shell catalyst can be performed at 800° C. or more and 1500° C. or less in a reducing atmosphere (of hydrogen or the like).

Then, the PtCo alloy or the PtCoMn alloy used as the core is subjected to the treatment for forming a Pt shell layer. An example of the treatment for forming a shell layer includes a treatment for causing the core of the PtCo alloy or the PtCoMn alloy to come into contact with an oxidizing solution (oxidizing solution treatment). When the oxidizing solution is contacted with the Pt alloy core, cobalt and manganese present on the surface of the Pt alloy elute with platinum caused to remain on the surface, and thus, the shell layer is formed. Examples of the oxidizing solution include solutions of sulfuric acid, nitric acid, phosphorus acid, potassium permanganate, hydrogen peroxide, hydrochloric acid, chloric acid, hypochlorous acid, and chromic acid. A concentration of the oxidizing solution is preferably 0.1 to 1 mol/L. The oxidizing solution treatment can be performed once, or a plurality of times.

As the treatment for forming the shell layer on the surface of the Pt alloy, a treatment for causing the Pt alloy (core) to come into contact with a platinum compound solution (platinum compound solution treatment) may be performed. In this platinum compound solution treatment, a platinum layer is formed through a substitution reaction with the metals (platinum, cobalt, and manganese) on the surface of the Pt alloy (core). Examples of the platinum compound solution suitably used in this treatment include a dinitrodiammineplatinum nitrate solution, a chloroplatinate aqueous solution, and a potassium chloroplatinate aqueous solution.

It is noted that the platinum compound solution treatment may be performed on the Pt alloy having been subjected to the oxidizing solution treatment described above.

Through the procedures for supporting the various metals on the carrier (solution impregnation/reduction/heat treatment) and forming the platinum shell layer described above, the core-shell catalyst of the present invention can be produced. As the carrier used here, a carbon fine powder carrier having the above-described prescribed specific surface area can be suitably used, and a carbon fine powder carrier having hydrophilicity is more preferably used. When a sufficiently hydrophilic carrier is used, platinum can be more finely and more highly dispersively supported in the process of impregnation with the platinum salt solution (process for supporting platinum salt). Thus, a core particle in a preferred state is formed, and a platinum shell layer formed thereafter is also preferred. As a treatment for improving hydrophilicity of the carbon fine powder carrier (hydrophilic treatment), a method in which the carbon fine powder carrier is wet ground in water before supporting the various metals can be employed. Here, the wet grinding is preferably performed with a homogenizer, or using zirconia beads as a grinding medium. Besides, a treatment time is preferably 10 minutes or more and 1 hour or less.

(B) Method for Designing Catalyst for Oxygen Reduction Reaction of Invention

Next, an embodiment of a method for designing a catalyst for an oxygen reduction reaction of the present invention will be described.

Figure 1A:
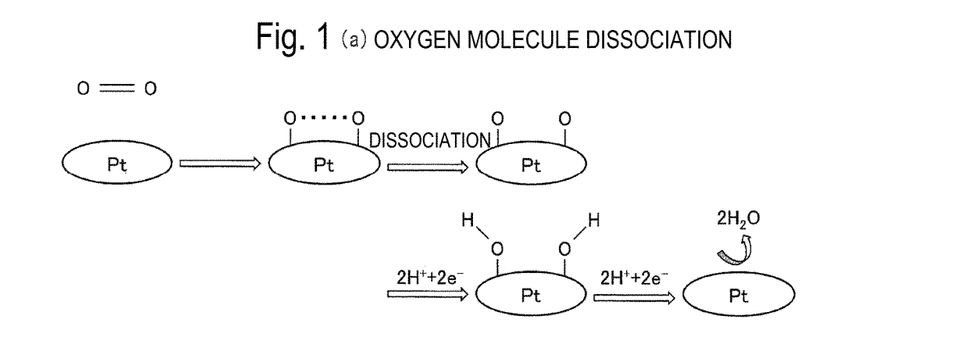
FIGS. 1(a)-1(c) are a model diagram illustrating a reaction mechanism of an oxygen reduction reaction.
Figure 1B:
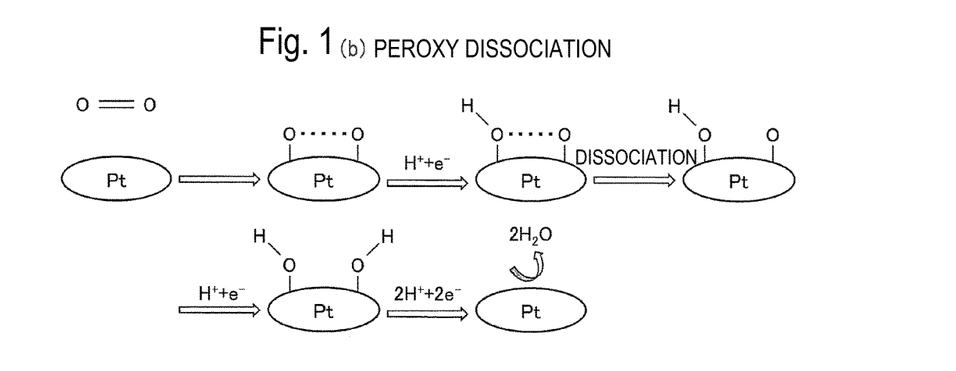
Figure 1C:
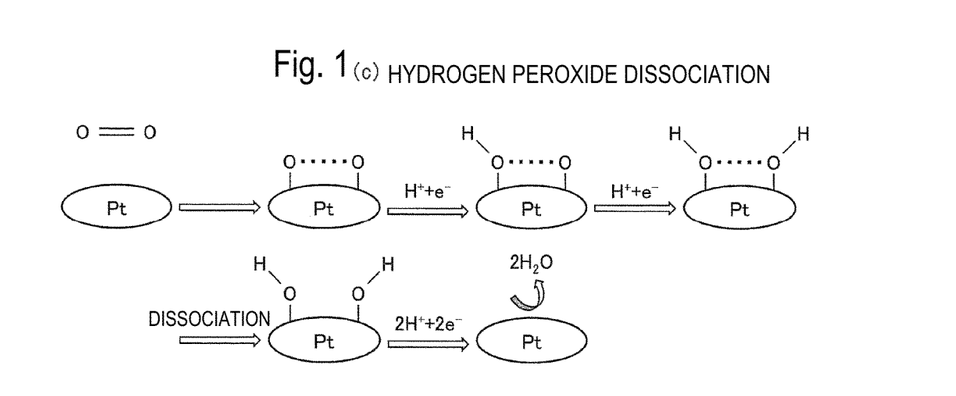

The present invention relates to catalyst design for promoting an oxygen reduction reaction, and therefore, it is necessary to first set a mechanism of an oxygen reduction reaction. As illustrated in FIGS. 1(a)-1(c), as a reaction model for an oxygen reduction reaction, three patterns of reaction paths, that is, FIG. 1(a) oxygen molecule dissociation, FIG. 1(b) peroxy dissociation, and FIG. 1(c) hydrogen peroxide dissociation, are known. In an oxygen reduction reaction in a fuel cell cathode or the like, it is presumed that these reaction paths singly or multiply proceed. In each of the reaction paths, however, three processes of (1) oxygen molecule adsorption process, (2) OH group (hydroxy group) generation process through a reaction between an oxygen atom and a proton, and (3) water molecule generation/desorption process are necessary for promoting the oxygen reduction reaction. Therefore, in the catalyst design, it is preferable to simulate, as a reaction energy related to each of the processes, (1) oxygen molecule adsorption energy, (2) OH adsorption energy, and (3) water molecule adsorption energy (energy working as a barrier to water molecule desorption). In a core-shell catalyst, these reaction energies vary depending on the types and compositions of the alloy elements of the Pt alloy used as a core. Therefore, the reaction energy in each process is estimated with respect to each alloy element, and alloy elements capable of obtaining numerical values advantageous over a Pt catalyst are selected, and thus, a catalyst superior to the Pt catalyst can be designed.

In the estimation of the respective reaction energies, simulation using first-principles calculation based on density functional theory is performed. The first-principles calculation refers to a calculation method based on density functional theory indicating that "energy in a ground state of interactive multi-electron system is determined based on an electron density distribution". According to first-principles calculation, an electron structure of a substance can be quantitatively discussed without using experimental parameters. Besides, in this simulation, generalized gradient approximation (GGA) that is currently the most accurate in the first-principles calculation is preferably used. Through the simulation using the first-principles calculation based on density functional, evaluation similar to experimental verification can be performed. A specific method of the simulation performed in the catalyst design method of the present invention will now be described.

(I) Selection of Orientation Plane Formed by Platinum Atoms

Platinum is a metal having an fcc structure (face-centered cubic lattice), and platinum atoms contained in the shell layer can form the (111) plane, the (001) plane, and the (110) plane of the fcc structure. In the simulation performed in the design method of the present invention, any one of the orientation planes is selected as the orientation plane formed by platinum atoms. In this regard, it has been reported that the (110) plane has a large surface energy and is chemically unstable as compared with the other planes (Patent Document 3), and therefore, the other planes are preferably selected as a target priorly to the (110) plane. Besides, it has been conventional reported that reaction activity of platinum on the orientation plane is better on the (111) plane than on the (001) plane. Accordingly, the (111) plane is preferably priorly selected as the orientation plane for the platinum shell layer. On the basis of this knowledge, the core-shell catalyst of the present invention also uses the (111) plane as the orientation plane formed by platinum atoms. It is not clear how the composition of the Pt alloy contained in the core affects, and hence, the (001) plane or the (110) plane may be selected as a target of the simulation, or a plurality of orientation planes may be selected for performing the simulation. Herein, the orientation plane of the (111) plane is selected as arrangement of platinum atoms.

In the simulation of the present invention, calculation is performed not only on the core-shell catalysts (the Pt/PtCo catalyst and the Pt/PtCoMn catalyst) of the present invention but also on the Pt catalyst for comparison. As a condition for the simulation, each catalyst is a catalyst consisting of 6 atomic layers. Specifically, each of the Pt/PtCo catalyst and the Pt/PtCoMn catalyst is presumed to have a structure in which a Pt atom, a Co atom, and a Mn atom are arranged in 5 atomic layers (from a sixth layer to a second layer), and a single atomic layer of a Pt atom is stacked thereon as a first layer. In the core-shell catalyst, however, the thickness of the platinum layer used as the shell layer is not limited to a single atomic layer. The Pt/PtCo catalyst and the Pt/PtCoMn catalyst respectively have core structures of $Pt_3Co$ (x=0.33), and $Pt_3Co_{0.8}Mn_{0.2}$ (y=0.27 and z is 0.067).

(II) Calculation of Reaction Energy in Each Process of ORR

Next, the reactions in the processes (1) to (3) described above in platinum atoms on the selected orientation plane are simulated to calculate reaction energies.

(II-1) Oxygen Molecule Adsorption Process (II-1-1) Oxygen Atom Adsorption Energy Energy in adsorption of an oxygen molecule onto the catalyst surface as the first process of ORR is calculated. Here, before describing the simulation of oxygen molecule adsorption, a case of an oxygen atom adsorbing onto a catalyst surface will be described. When an oxygen molecule adsorbs onto a catalyst surface, there are a large number of forms depending on the positional relationship between a platinum atom and a cobalt/manganese atom. Therefore, it is decided to simulate a preferential oxygen atom adsorption site on the catalyst surface to examine possible forms of adsorption of an oxygen molecule.

Figure 2:
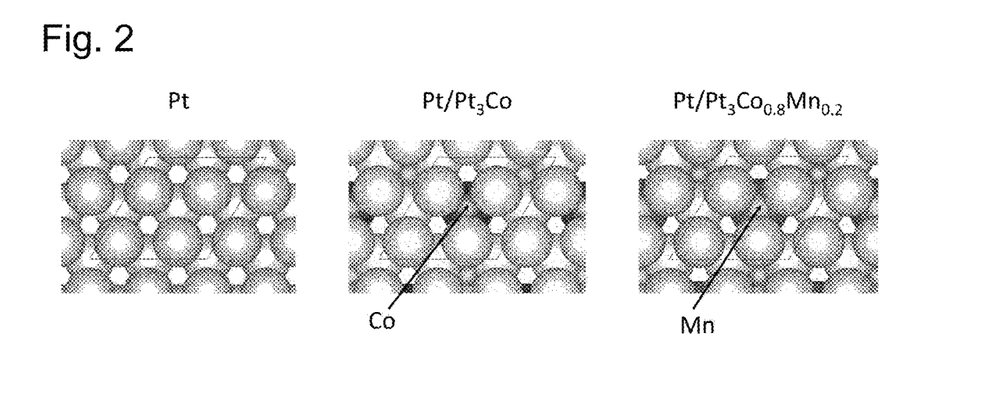
FIG. 2 is a diagram of the (111) plane of an fcc structure viewed from a normal direction.

FIG. 2 is a diagram of each of the Pt catalyst, the Pt/PtCo catalyst and the Pt/PtCoMn catalyst viewed from a normal direction of the (111) plane when platinum atoms form the (111) plane of the fcc structure. As illustrated in FIG. 2, Co is disposed in the second layer below the first layer in the Pt/PtCo catalyst, and Mn is disposed in the second layer below the first layer in the Pt/PtCoMn catalyst.

Figure 3:
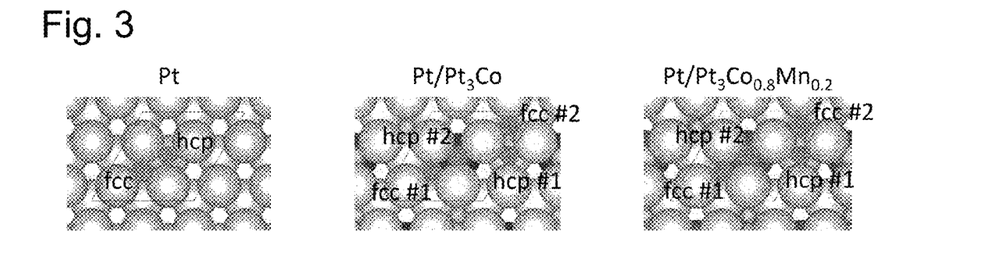
FIG. 3 is a diagram illustrating oxygen atom adsorption sites on surfaces of a Pt catalyst, a Pt/PtCo catalyst, and a Pt/PtCoMn catalyst.

As illustrated in FIG. 3, oxygen atom adsorption sites presumed to have high preference on the (111) plane of the fcc structure of the Pt catalyst or the like are two adsorption sites present in a position surrounded by three atoms (hollow), specifically, an hcp hollow site (indicated as hcp in FIG. 3; hereinafter sometimes referred to as the h site), and an fcc hollow site (indicated as fcc in FIG. 3; hereinafter sometimes referred to as the f site). The h site is an adsorption site present in a hollow (dimple) positioned on an atom of the second layer when viewed from the normal direction in FIG. 3. The f site is an adsorption site present in a hollow positioned on a position surrounded by atoms of the second layer (hollow) when viewed from the normal direction in FIG. 2. In addition to the h site and the f site, possible adsorption sites for an oxygen atom include a top site (t site) positioned on a platinum atom, and a bridge site (b site) positioned between two platinum atoms, but these sites are excluded from the target of the simulation on an oxygen atom because it has been cleared through examination and the like made beforehand by the present inventions that these adsorption sites have low oxygen atom adsorption energy.

Also in the Pt/PtCo catalyst and the Pt/PtCoMn catalyst, the oxygen atom adsorption sites are basically the h site and the f site. In a catalyst using a Pt alloy (a PtCo alloy or a PtCoMn alloy) as a core, however, each of these two adsorption sites is further classified into two sites depending on the positional relationship between Co and Mn in the second layer. Specifically, the h site is classified into an hcp #1 site as an h site positioned on a Pt atom of the second layer, and an hcp #2 site as an h site positioned on a Co atom (or Mn atom) of the second layer. Besides, the f site is classified into an fcc #1 site as an f site positioned close to a Co atom (or Mn atom) of the second layer, and an fcc #2 site as an f site positioned away from a Co atom (or Mn atom) of the second layer. It is noted that the t site and the b site are excluded in the adsorption simulation for an oxygen atom also in the Pt/PtCo catalyst and the Pt/PtCoMn catalyst for the same reason as that for the Pt catalyst.

Then, regarding the respective adsorption sites, oxygen atom adsorption energy is obtained. Here, for the calculation of the adsorption energy, a difference between an energy ($E_0$) obtained when an oxygen atom is present in a position at infinity from the catalyst surface and an energy (E) obtained when an oxygen atom adsorbs onto the catalyst surface ($\Delta E = E - E_0$) is obtained. Calculation results thus obtained are shown in Table 1.

TABLE 1

|  | hcp | | fcc | |
| --- | --- | --- | --- | --- |
|  | hcp#1 | hcp#2 | fcc#1 | fcc#2 |
| Pt |  | −0.83 |  | −1.27 |
| Pt/PtCo | −0.48 | −0.47 | −0.88 | −0.60 |
| Pt/PtCoMn | −0.46 | −0.51 | −0.89 | −0.38 | unit: eV

The magnitude of the adsorption energy is evaluated based on the absolute value thereof. As is understood from Table 1, the adsorption energy is the maximum in the fcc site in all of the Pt, Pt/PtCo and Pt/PtCoMn catalysts. In the Pt/PtCo and Pt/PtCoMn catalysts, the adsorption energy is maximum in the fcc #1 site. It is understood from these calculation results that adsorption in the fcc #1 site is stable in both the Pt/PtCo and Pt/PtCoMn catalysts when an oxygen atom adsorbs onto the catalyst surface in the (111) plane of the fcc structure formed by platinum atoms.

(II-1-2) Oxygen Molecule Adsorption Energy

In consideration of these adsorption models for an oxygen atom, a model for an oxygen molecule adsorbing onto the catalyst surface in the (111) plane of the fcc structure formed by platinum atoms will now be examined. For oxygen molecule adsorption site, it is necessary to consider three adsorption sites of two oxygen atoms and the center of gravity therebetween. Here, the adsorption sites of two oxygen atoms and the center of gravity therebetween can be a top site (t site), a bridge site (b site), an hcp hollow site (h site), and an fcc site. In the Pt/PtCo and Pt/CoMn catalysts, each of these adsorption sites is classified into two, that is, t #1 and t #2 sites, b #1 and b #2 sites, t #1 and t #2 sites or the like based on the positional relationship with Co and Mn in the second layer.

Figure 4:
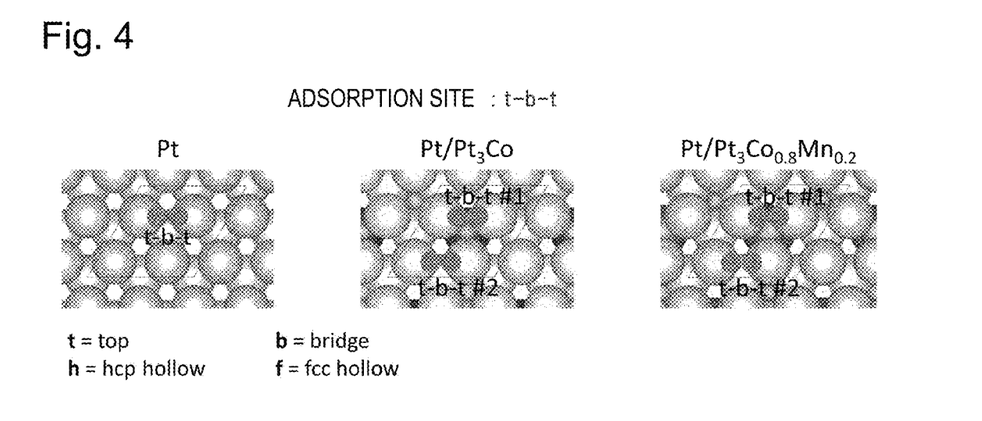
FIG. 4 is a diagram illustrating oxygen molecule adsorption sites (t-b-t) on surfaces of a Pt catalyst, a Pt/PtCo catalyst, and a Pt/PtCoMn catalyst.
Figure 5:
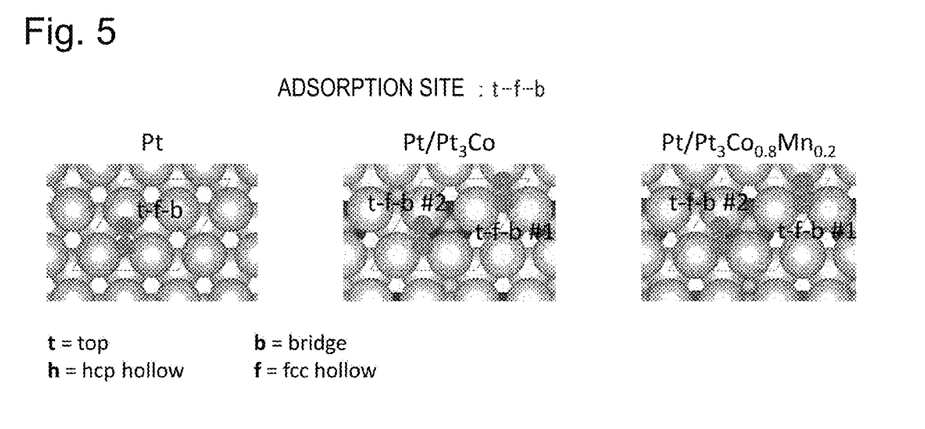
FIG. 5 is a diagram illustrating oxygen molecule adsorption sites (t-f-t) on surfaces of a Pt catalyst, a Pt/PtCo catalyst, and a Pt/PtCoMn catalyst.
Figure 6:
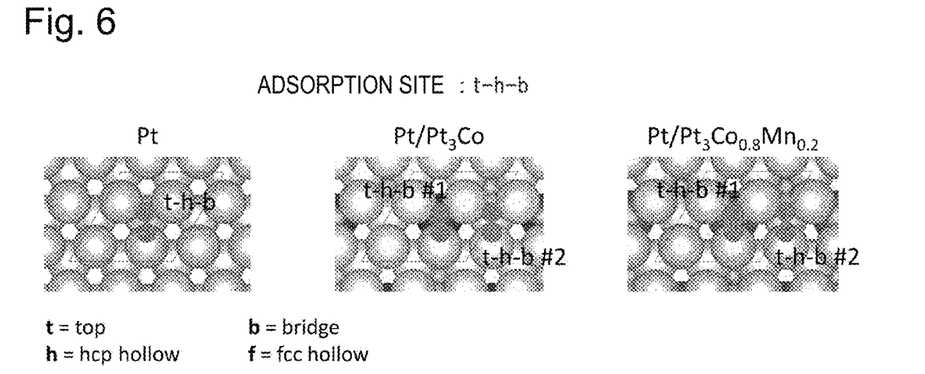
FIG. 6 is a diagram illustrating oxygen molecule adsorption sites (t-h-b) on surfaces of a Pt catalyst, a Pt/PtCo catalyst, and a Pt/PtCoMn catalyst.

According to literatures, the oxygen molecule adsorption sites in the (111) plane formed by platinum atoms are dominantly three sites of t-b-t, t-f-b, and t-h-b sites (A. Eichler, J. Hafner, Phys. Rev. Lett. 79 (1997) 4481-4484) and M. M. Montemore, M. A. Spronsen, R. J. Madix, C. M. Friend, Chem. Rev. 118 (2018) 2816-2862). Based on this knowledge, oxygen molecule adsorption patterns onto the respective adsorption sites are as illustrated in FIG. 4, FIG. 5 and FIG. 6 when the (111) plane of the fcc structure is formed by platinum atoms in the Pt catalyst, the Pt/PtCo catalyst, and the Pt/PtCoMn catalyst.

Therefore, oxygen molecule adsorption energies in the respective adsorption sites are obtained. Here, for the calculation of the oxygen molecule adsorption energy, a difference between an energy ($E_0$) obtained when an oxygen molecule is present in a position at infinity from the catalyst surface and an energy (E) obtained when an oxygen molecule adsorbs onto the catalyst surface ($\Delta E = E - E_0$) is obtained. Calculation results thus obtained are shown in Table 2.

TABLE 2

|  | t-b-t | | t-f-b | | t-h-b | |
| --- | --- | --- | --- | --- | --- | --- |
|  | t-b-t#1 | t-b-t#2 | t-f-b#1 | t-f-b#2 | t-h-b#1 | t-h-b#2 |
| Pt |  | −0.75 |  | −0.77 |  | −0.65 |
| Pt/PtCo | −0.39 | −0.43 | −0.39 | −0.35 | −0.39 | −0.28 |
| Pt/PtCoMn | −0.39 | −0.38 | −0.40 | −0.35 | −0.39 | −0.30 | unit: eV

It is understood from Table 2 that the adsorption energy values are close in the t-b-t site and the t-f-b site, and that the adsorption energy is larger in these sites than in the t-h-b site. Therefore, when the (111) plane of the fcc structure is formed by platinum atoms in the Pt catalyst, the Pt/PtCo catalyst, and the Pt/PtCoMn catalyst, an oxygen molecule is found to be likely to adsorb onto the t-b-t site and the t-f-b site.

In the Pt/PtCo catalyst and the Pt/PtCoMn catalyst, the absolute value of the adsorption energy in an adsorption site having the maximum oxygen atom adsorption energy is preferably less than 1.0 eV, and the absolute value of the adsorption energy in an adsorption site having the maximum oxygen molecule adsorption energy is preferably less than 0.5 eV.

(II-1-3) Dissociation Adsorption from Oxygen Molecule to Oxygen Atom

Figure 7:
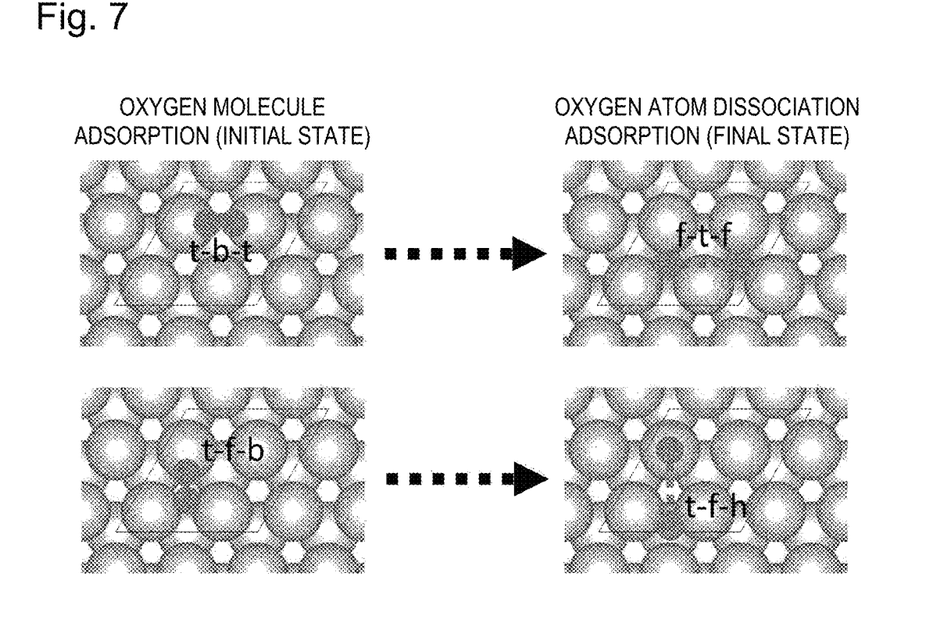
FIG. 7 is a diagram illustrating oxygen molecules adsorbed onto a t-b-t site and a t-f-b site on a surface of catalysts (initial state), and a final state of oxygen atoms having been dissociated/rearranged.

An oxygen molecule having adsorbed onto the catalyst surface dissociates to an oxygen atom and adsorbs for generation of a hydroxy group, that is, the next process. As described above, when the (111) plane of the fcc structure is formed by platinum atoms, an oxygen molecule adsorbs onto the t-b-t site and the t-f-b site. Oxygen molecules having adsorbed onto these adsorption sites dissociate to oxygen atoms, and rearrange with mutually increasing interatomic distances. FIG. 7 illustrates models of oxygen molecules adsorbed onto the t-b-t site and the t-f-b site (initial state), and a final state where the oxygen molecules have dissociated to oxygen atoms and rearranged. A path from the initial state to the final state, and activation energy can be calculated by simulation to which CI-NEB (climbing image-nudged elastic band) method is applied. NEB method is a method for analyzing a transition path of a target reaction based on structures in the initial state and the final state. According to NEB method, the activation energy of the reaction can be obtained based on an energy curve along the transition path.

Figure 8:
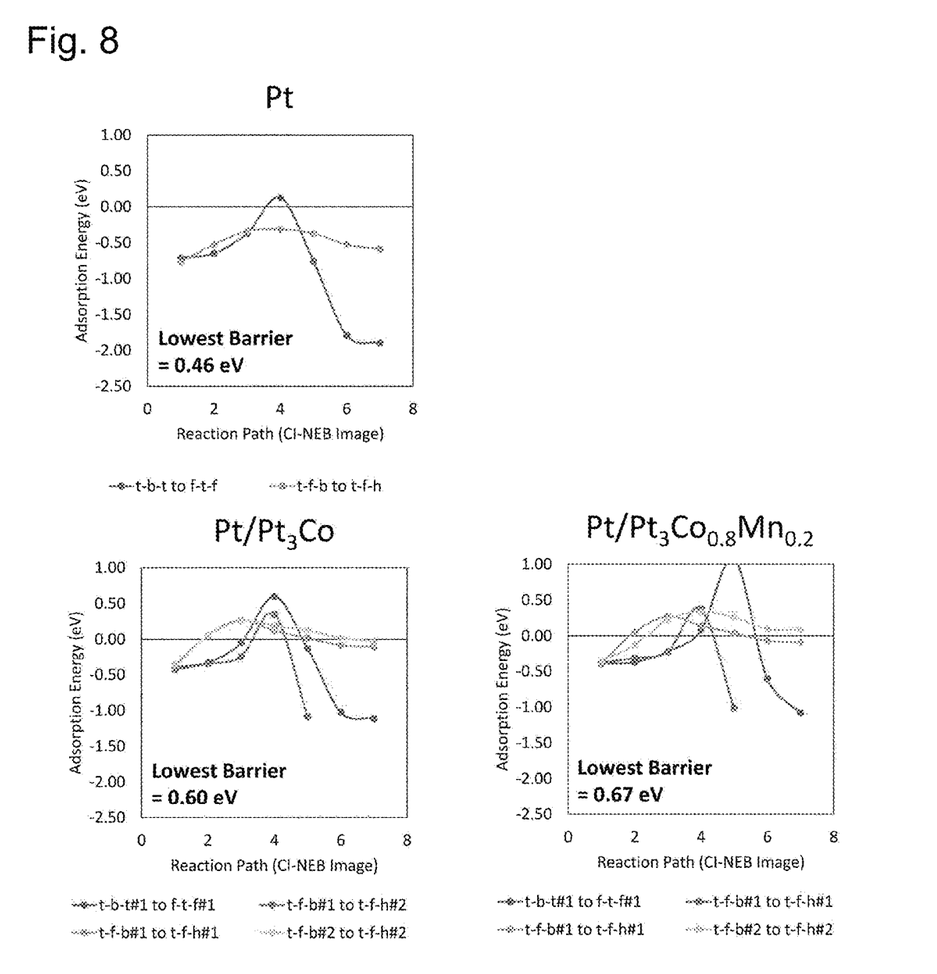
FIG. 8 is a diagram illustrating simulation results of activation energy obtained dissociation of oxygen molecules in a Pt catalyst, a Pt/PtCo catalyst, and a Pt/PtCoMn catalyst.

FIG. 8 illustrates simulation results of activation energies of dissociation, to an oxygen atom, of an oxygen molecule having adsorbed onto the (111) plane formed by platinum atoms in the Pt catalyst, the Pt/PtCo catalyst, and the Pt/PtCoMn catalyst. Through the analysis of the simulation results by the present inventors, the following is calculated as activation barriers in the dissociation reaction of oxygen atoms in the respective catalysts. As shown in Table 3 below, the activation barrier is lowest in the Pt catalyst, and lower in the order of the Pt/PtCo catalyst and the Pt/PtCoMn catalyst.

TABLE 3

|   | Activation Barrier (eV) |
|---|---|
| Pt | 0.46 |
| Pt/PtCo | 0.60 |
| Pt/PtCoMn | 0.67 |

(2) OH Generation Process

Figure 9:
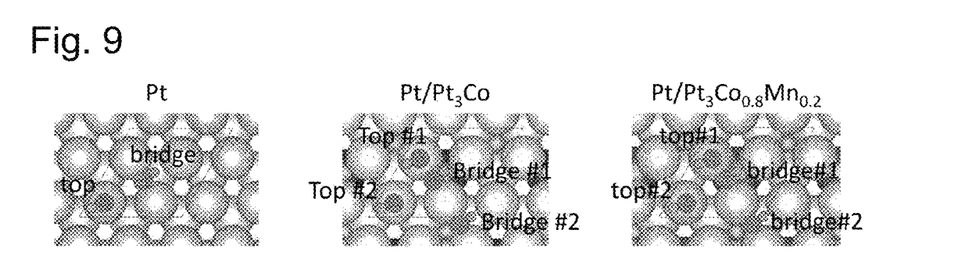
FIG. 9 is a diagram illustrating OH adsorption sites on surfaces of a Pt catalyst, a Pt/PtCo catalyst, and a Pt/PtCoMn catalyst.

For example, in a cathode of a fuel cell, a proton is supplied to the cathode from an anode side via a solid electrolyte. After the dissociation adsorption of oxygen molecules described above, OH is generated with the proton supply. FIG. 9 is a diagram illustrating adsorption sites for the thus generated OH. In the Pt catalyst, the Pt/PtCo catalyst, and the Pt/PtCoMn catalyst, OH predominantly adsorbs onto top sites (top #1 and #2 sites) and bridge sites (bridge #1 and #2 sites) on the (111) plane formed by platinum atoms.

In these adsorption sites, OH adsorption energies are obtained. Here, for the calculation of the adsorption energy, a difference between an energy ($E_0$) obtained when OH is present in a position at infinity from a catalyst surface and an energy (E) obtained when OH adsorbs onto the catalyst surface ($\Delta E = E - E_0$) is obtained. Calculation results thus obtained are shown in Table 4. Referring to Table 4, an absolute value of an adsorption energy in an adsorption site having a maximum OH group adsorption energy is less than 2.3 eV in the Pt/PtCo catalyst and the Pt/PtCoMn catalyst.

TABLE 4

|  | top | | bridge | |
|---|---|---|---|---|
|  | top#1 | top#2 | bridge#1 | bridge#2 |
| Pt |  | −2.38 |  | −2.41 |
| Pt/PtCo | −2.15 | −2.22 | −2.12 | −2.03 |
| Pt/PtCoMn | −2.14 | −2.20 | −2.13 | −1.89 | unit: eV (3) Water Molecule Generation/Desorption Process

Figure 10:
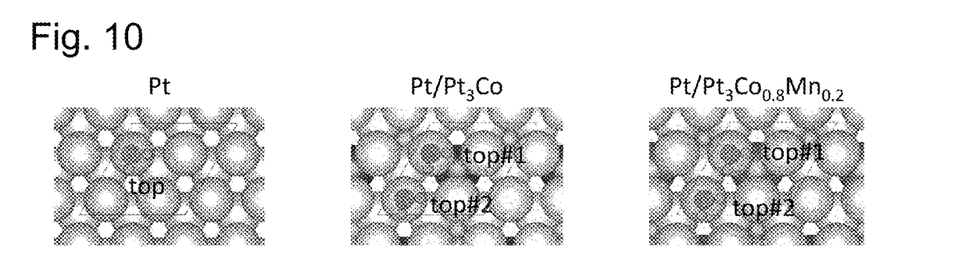
FIG. 10 is a diagram illustrating water molecule adsorption sites on surfaces of a Pt catalyst, a Pt/PtCo catalyst, and a Pt/PtCoMn catalyst.

Then, the OH thus generated on the catalyst surface reacts with the proton, resulting in generating/desorbing water. FIG. 10 is a diagram illustrating adsorption sites of a water molecule thus generated. In the Pt catalyst, the Pt/PtCo catalyst, and the Pt/PtCoMn catalyst, a water molecule predominantly adsorbs onto top sites (top #1 and #2 sites) on the (111) plane formed by platinum atoms.

Then, in these adsorption sites, water adsorption energies are obtained. Here, for the calculation of the adsorption energy, a difference between an energy ($E_0$) obtained when water is present in a position at infinity from a catalyst surface and an energy (E) obtained when water adsorbs onto the catalyst surface ($\Delta E = E - E_0$) is obtained. Calculation results thus obtained are shown in Table 5. Referring to Table 5, an absolute value of an absorption energy in an adsorption site having a maximum water molecule adsorption energy is less than 0.19 eV in the Pt/PtCo catalyst and the Pt/PtCoMn catalyst.

TABLE 5

|  | top | |
|---|---|---|
|  | top#1 | top#2 |
| Pt |  | −0.21 |
| Pt/PtCo | −0.17 | −0.13 |
| Pt/PtCoMn | −0.17 | −0.12 | unit: eV (III) Density of States on Each Catalyst Surface

Figure 11:
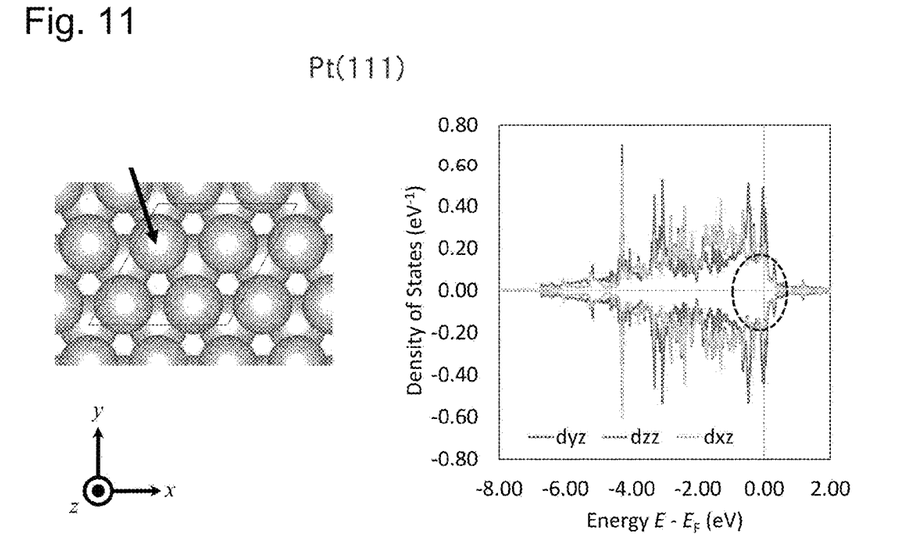
FIG. 11 is a diagram illustrating density of states on the (111) plane of a Pt catalyst.
Figure 12:
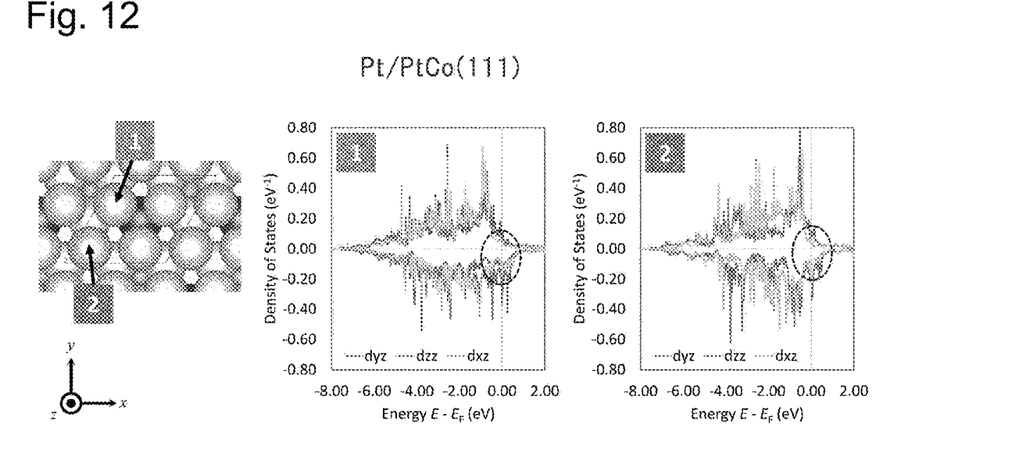
FIG. 12 is a diagram illustrating density of states on the (111) plane of a Pt/PtCo catalyst.
Figure 13:
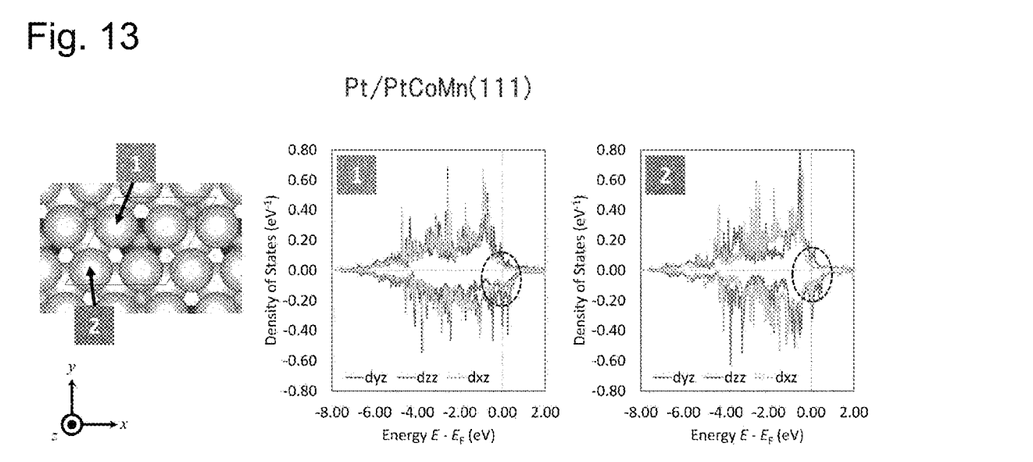
FIG. 13 is a diagram illustrating density of states on the (111) plane of a Pt/PtCoMn catalyst.

In addition to the simulation of the above-described respective reaction processes in ORR, the present inventors simulated a density of states on the (111) plane of the face-centered cubic lattice formed by platinum atoms in the Pt catalyst, the Pt/PtCo catalyst and the Pt/PtCoMn catalyst by using first-principles calculation based on density functional theory. Results are illustrated in FIG. 11, FIG. 12 and FIG. 13. In these drawings, an orbital having a low density of states is omitted, and notable three 5d orbitals dxy, dyz, and dzz are illustrated. Besides, in the Pt/PtCo catalyst and the Pt/PtCoMn catalyst, the simulation is performed on two positions in consideration of the positional relationship with a Co atom and Mn atom in the second layer.

Referring to the simulation results of the Pt catalyst illustrated in FIG. 11, the electron density is high in the vicinity of the Fermi level ($E - E_F = 0$). This indicates that the Pt catalyst exhibits preferred catalytic activity.

The simulation results of the Pt/PtCo catalyst and the Pt/PtCoMn catalyst respectively illustrated in FIG. 12 and FIG. 13 will be examined in comparison with the Pt catalyst. In these catalysts, the peaks of density of states are high as a whole, and there is a peak shift to the Fermi level. In particular, the peak of the dxz orbital is high and sharp in the vicinity of the Fermi level ($E - E_F = 0$ to $-1.0$ eV). It is known that the dxz orbital predominantly acts on an O—Pt bond. Therefore, it is estimated that the Pt/PtCo catalyst and the Pt/PtCoMn catalyst exhibit high catalytic activity as compared with the Pt catalyst, and have a large binding force with oxygen on the catalyst surface.

(IV) Electrode Potential in ORR

The oxygen reduction reaction (ORR) is completed through (1) the oxygen molecule adsorption (dissociation adsorption) process, (2) the OH generation process and (3) the water molecule generation/desorption process described above. Here, reaction formulas at the respective stages in the ORR are as follows:

Formula 1

$$\tfrac{1}{2}\cdot O_2 + \text{surface} \rightarrow O_{ads} \qquad (1)$$

$$O_{ads} + (H^+ + e^-) \rightarrow OH_{ads} \qquad (2)$$

$$OH_{ads} + (H^+ + e^-) \rightarrow H_2O + \text{surface} \qquad (3)$$

Figure 14:
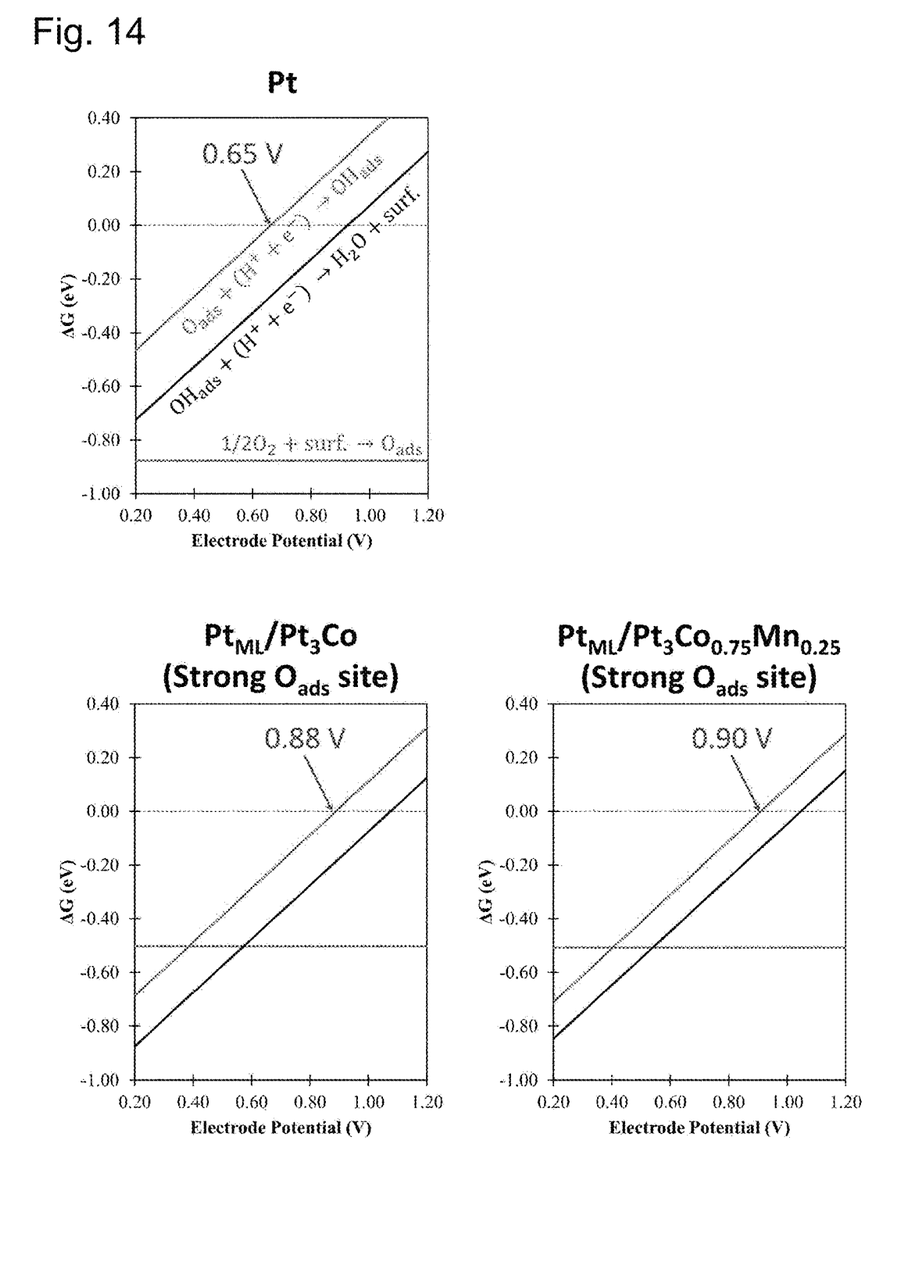
FIG. 14 is a diagram illustrating simulation results of electrode potentials in an oxygen reduction reaction of a Pt catalyst, a Pt/PtCo catalyst, and a Pt/PtCoMn catalyst.

In the reaction formulae, the oxygen adsorption of the formula (1) is a chemical reaction, and the OH generation reaction of the formula (2) and the water generation reaction of the formula (3) are electrochemical reactions (protonation). According to the density functional theory, an electrode potential in ORR can be simulated. FIG. 14 illustrates simulation results of electrode potentials in the reactions of the formulas (1) to (3) in the Pt catalyst, the Pt/PtCo catalyst, and the Pt/PtCoMn catalyst. Referring to FIG. 14, theoretical values of the electrode potentials in the respective catalysts are as follows.

TABLE 6

|  | Electrode Potential (V) |
| --- | --- |
| Pt | 0.65 |
| Pt/PtCo | 0.88 |
| Pt/PtCoMn | 0.90 |

It is thus understood that the electrode potentials in using the Pt/PtCo catalyst and the Pt/PtCoMn catalyst are higher than that in using the Pt catalyst. Therefore, it is understood, also from the results of this simulation, that the Pt/PtCoMn catalyst exhibits high catalytic activity as compared with the Pt catalyst.

From the results of the various simulations on ORR based on the density functional theory described above, it is understood that the respective energies significant in the reaction processes of ORR (the oxygen molecule adsorption energy, the OH adsorption energy and the water molecule adsorption energy) are all lower in the Pt/PtCo catalyst and the Pt/PtCoMn catalyst than in the Pt catalyst. This probably relates to high activity in ORR. Besides, it is confirmed, also from the simulation results on the density of states and the electrode potential in ORR, that the Pt/PtCo catalyst and the Pt/PtCoMn catalyst have high activity.

Although the present embodiment relates to the catalyst design based on the simulations of a core-shell catalyst using a PtCo alloy or a PtCoMn alloy as a core, a similar design method can be applied also to a core-shell catalyst including a core containing an alloy element different from Co and Mn.

EXAMPLES

Regarding the embodiment of the present invention described above, specific examples will now be described. In these examples, a core-shell catalyst containing a PtCo alloy or a PtCoMn alloy having a prescribed composition as a core, and a platinum shell layer was produced to be compared with a Pt catalyst in activity.

Example 1 (Pt/PtCo Catalyst)

In this example, a Pt catalyst was first produced, a core was formed by supporting cobalt thereon to obtain an alloy, and the resultant was subjected to an oxidizing solution treatment and a platinum compound solution treatment to produce a Pt/PtCo catalyst. Before producing the Pt catalyst, a carbon fine powder (with a specific surface area of 850 m²/g) to be used as a carrier was prepared, and was subjected to a wet grinding treatment for hydrophilizing the carrier. The wet grinding of the carrier was performed with a homogenizer at 700 rpm for 10 minutes with 2 L of water used per 50 g of the carbon fine powder.

A production vessel was charged with 46 g of the hydrophilized carbon fine powder, 1000 g of a dinitrodiammineplatinum nitrate solution, used as a platinum salt solution, having a platinum concentration of 4.6% by mass (platinum content: 46 g). Thereafter, 540 mL of 100% ethanol was added as a reducing agent to be mixed. The thus obtained mixed solution was refluxed at about 85° C. for 4 hours to reduce platinum. Thereafter, the resultant was filtered, dried and washed.

Next, cobalt was supported on the Pt catalyst. As a metal salt solution, a metal salt solution containing 100 g of cobalt chloride hexahydrate (CoCl₂·6H₂O) dissolved in 500 mL of water was produced, and the Pt catalyst was immersed and mixed therein. Then, to the resultant solution, 10 L of a sodium borohydride solution with a concentration of 1% by mass was added in a dropwise manner, the resultant was stirred to perform a reduction treatment, and thus, cobalt was supported on the Pt catalyst. Thereafter, the resultant was filtered/washed/dried. Then, a heat treatment was performed to obtain an alloy. The heat treatment was performed in 100% hydrogen gas at a heat treatment temperature of 900° C. for 0.5 hours. Thus, a precursor catalyst containing a PtCo alloy core formed on the carbon fine powder carrier was obtained.

The precursor catalyst was subjected to an oxidizing solution treatment and a platinum compound solution treatment. First, the precursor catalyst was treated in a 0.5 mol/L sulfuric acid aqueous solution at 80° C. for 2 hours, and the resultant was filtered/washed/dried. Then, the resultant was treated in a 1.0 mol/L nitric acid aqueous solution at 70° C. for 2 hours, and the resultant was filtered/washed/dried. This treatment with the nitric acid aqueous solution was performed twice.

Then, the precursor catalyst having been subjected to the oxidizing solution treatment was treated with a platinum compound solution. Here, a solution obtained by diluting 11.9 g of chloroplatinic acid (platinum: 1.78 g) with pure water 2.5-fold was prepared as the platinum compound solution. In the platinum compound solution treatment, 1 L of a 1M hydrochloric acid aqueous solution was first prepared per 10 g of the catalyst, and the catalyst was dispersed in the hydrochloric acid aqueous solution to obtain a slurry. Then, to the slurry of the precursor catalyst thus obtained, the chloroplatinic acid solution was added in a dropwise manner (10 mL/min). After the dropwise addition, the resultant was stirred for 24 hours, and then filtered and washed repeatedly three times. Ultimately, the resultant was dried at 60° C. for 24 hours.

Example 2 (Pt/PtCoMn Catalyst)

A Pt/PtCoMn catalyst was produced by supporting cobalt and manganese on the Pt catalyst produced in Example 1.

The Pt catalyst was immersed in a metal salt solution, which was obtained by dissolving cobalt chloride ($CoCl_2 \cdot 6H_2O$) and manganese chloride ($MnCl_2 \cdot 4H_2O$) in 100 mL of ion-exchanged water, to be impregnated with the solution by stirring. To the resultant solution, 500 mL of a sodium borohydride solution with a concentration of 1% by mass was added in a dropwise manner to perform a reduction treatment by stirring. Then, a heat treatment was performed for obtaining an alloy. The heat treatment was performed in 100% hydrogen gas at a heat treatment temperature of 900° C. for 0.5 hours. Thus, a precursor catalyst containing a PtCoMn alloy core formed on the carbon fine powder carrier was obtained. Besides, the precursor catalyst was subjected to the oxidizing solution treatment and the platinum compound solution treatment under the same conditions as those employed in Example 1.

Comparative Example (Pt Catalyst)

For comparison with the catalysts of Examples 1 and 2, the Pt catalyst used for producing the catalysts of the examples was prepared as an evaluation target.
[Structural Analysis of Catalyst Particle]
The compositions and lattice constants of catalyst particles of Example 1 (Pt/PtCo catalyst) and Example 2 (Pt/PtCoMn catalyst) thus produced were analyzed. In this structural analysis, 20 catalyst particles were arbitrarily selected in each of the catalysts for measuring the composition, and the lattice constants on the surface and inside. It is noted that the inside of a catalyst particle refers to a portion close to the center.

For the analysis of the composition of a catalyst particle, analysis by STEM-EDX was performed. As a result, it was confirmed that the composition of the Pt alloy core of the Pt/PtCo catalyst of Example 1 was $PtCo_{0.3}$. Besides, a Pt content on the surface was higher than a Pt content inside in the catalyst particle of this catalyst, and thus, it was confirmed that the catalyst had a core-shell structure. Next, the catalyst particle of the Pt/PtCo catalyst of Example 1 was analyzed by HAADF-STEM method, resulting in confirming that platinum atoms contained in the platinum shell layer of the catalyst particle were arranged on the (111) plane, and that surface 2 atomic layers corresponded to the platinum shell layer. Besides, the cross-section of the catalyst particle was analyzed by cs-STEM, resulting in finding that the lattice constant on the surface of the catalyst particle was 3.92 Å (on average). It was also confirmed that the lattice constants inside the respective catalyst particles were in a range of 3.70 Å or more and 4.05 Å or less. On the other hand, the lattice constant inside the catalyst particle was 3.76 Å (on average). It was confirmed that the lattice constants inside the respective catalyst particles were in a range of 3.55 Å or more and 3.95 Å or less.

The Pt/PtCoMn catalyst of Example 2 was analyzed in the same manner as in Example 1. As a result, it was confirmed that the composition of the Pt alloy core of the Pt/PtCoMn catalyst of Example 2 was $PtCo_{0.27}Mn_{0.067}$. In the same manner as in Example 1, a Pt content on the surface was higher than a Pt content inside in the catalyst particle, and thus, it was confirmed that the catalyst had a core-shell structure. Besides, it was confirmed, through the analysis by HAADF-STEM, that platinum atoms contained in the platinum shell layer were arranged on the (111) plane, and that surface 2 atomic layers corresponded to the platinum shell layer. It was confirmed through the analysis by cs-STEM that the lattice constant on the surface of the catalyst particle was 3.94 Å (on average). It was also confirmed that the lattice constants on the surfaces of the respective catalyst particles were in a range of 3.87 Å or more and 4.10 Å or less. On the other hand, the lattice constant inside the catalyst particle was 3.81 Å (on average). It was confirmed that the lattice constants on the surfaces of the respective catalyst particles were in a range of 3.70 Å or more and 4.05 Å or less.

As compared with the catalysts of Examples 1 and 2 described above, based on cs-STEM analysis of the catalyst particle of the Pt catalyst of Comparative Example, the lattice constant on the surface of the catalyst particle was 3.96 Å (on average), and the lattice constant inside the catalyst particle was 3.94 Å (on average). It was confirmed that the lattice constant was substantially the same on the surface and inside the catalyst particle in the Pt catalyst of Comparative Example.

Comparative Evaluation of ORR Activity

The catalysts of Examples 1 and 2 and Comparative Example were subjected to comparative evaluation of ORR activity. An evaluation test was performed by producing a single cell for performance evaluation on a cathode of a fuel cell, and measuring the mass activity of each catalyst. In the production of a single cell, a cathode electrode having an electrode area 5 cm×5 cm=25 cm² was first produced with use of each of the catalysts. Then, a proton conducting polymer electrolyte membrane was sandwiched between this cathode electrode and an anode electrode to produce a membrane electrode assembly (MEA). In the evaluation test, a current/voltage curve was drawn, as a pretreatment, under conditions of a hydrogen flow rate of 1000 mL/min, an oxygen flow rate of 1000 mL/min, a cell temperature of 80° C., an anode humidification temperature of 90° C., and a cathode humidification temperature of 30° C. Thereafter, the mass activity was measured as main measurement. As a test method, a current value (A) at 0.9 V was measured to obtain a current value (A/g-Pt) per g of Pt based on the weight of Pt applied on the electrode, which was used for calculating the mass activity. Then, on the basis of the mass activity of the Pt catalyst, the mass activities of the Pt/PtCo catalyst and the Pt/PtCoMn catalyst were relatively evaluated. Results of this activity evaluation test are shown in Table 7.

TABLE 7

| | Mass Activity[*1] |
|---|---|
| Example 1 (Pt/PtCo) | 1.7 |
| Example 2 (Pt/PtCoMn) | 2.0 |
| Comparative Example (Pt) | 1.0 |

[*1]relative evaluation assuming that Mass Activity of Pt catalyst is 1.0

It was confirmed from Table 7 that the Pt/PtCo catalyst (Example 1) and the Pt/PtCoMn catalyst (Example 2) are excellent in ORR activity as compared with the Pt catalyst (Comparative Example). The Pt/PtCoMn catalyst had particularly high activity.

It was confirmed through this experimental verification that a core-shell catalyst containing a PtCo alloy or a PtCoMn alloy used as a core, and a platinum shell layer formed thereon has high activity in ORR. This result agrees with the calculation result obtained by the simulations based on density functional theory described above. For example, the simulation results of the electrode potential in ORR (Table 6) satisfactorily agree with the evaluation test results of Table 7. Accordingly, validity of the catalyst design method of the present invention was thus confirmed.

INDUSTRIAL APPLICABILITY

A catalyst for ORR of the present invention is a core-shell catalyst in which a preferred Pt alloy is used as a core, and has preferred activity in an oxygen reduction reaction. An example of specific and particularly preferred application of the present invention includes a cathode electrode of a fuel cell such as a polymer electrolyte fuel cell. Fuel cells are expected as next generation power generating systems for an automobile power supply and a household power supply, and have been put to practical use. The present invention contributes to trend of the practical application of such fuel cells. Besides, the present invention also discloses a catalyst design method through simulation based on density functional theory. In this catalyst design method, catalyst performances can be predicted/checked without performing experimental verification, and hence the method can make a contribution to efficiency improvement in designing/producing a preferred catalyst.

What is claimed is:

1. A catalyst for an oxygen reduction reaction, comprising catalyst particles having a core-shell structure containing a PtCo alloy as a core, and platinum as a shell layer,
   wherein a plurality of platinum atoms contained in the shell layer form a (111) plane of a face-centered cubic lattice,
   a lattice constant of the (111) plane of the face-centered cubic lattice on a surface of the catalyst particle is 3.70 Å or more and 4.05 Å or less, and
   a lattice constant of a (111) plane of the face-centered cubic lattice formed by platinum atoms present inside the catalyst particles is smaller than a lattice constant of a (111) plane of the face-centered cubic lattice on a surface of the catalyst particle.

2. The catalyst according to claim 1, wherein a lattice constant of a (111) plane of the face-centered cubic lattice formed by platinum atoms present inside the catalyst particles is 3.55 Å or more and 3.95 Å or less.

3. The catalyst according to claim 1, wherein the PtCo alloy contained in the core is $PtCo_x$, wherein $0.14 \leq x \leq 0.33$.

4. A catalyst for an oxygen reduction reaction, comprising catalyst particles having a core-shell structure containing a PtCoMn alloy as a core, and platinum as a shell layer,
   wherein a plurality of platinum atoms contained in the shell layer form a (111) plane of a face-centered cubic lattice,
   a lattice constant of the (111) plane of the face-centered cubic lattice on a surface of the catalyst particles is 3.870 Å or more and 4.10 Å or less, and
   a lattice constant of a (111) plane of the face-centered cubic lattice formed by platinum atoms present inside the catalyst particles is smaller than a lattice constant of a (111) plane of the face-centered cubic lattice on the surface of the catalyst particles.

5. The catalyst according to claim 4, wherein a lattice constant of a (111) plane of the face-centered cubic lattice formed by platinum atoms present inside the catalyst particles is 3.70 Å or more and 4.05 Å or less.

6. The catalyst according to claim 4, wherein the PtCoMn alloy contained in the core is $PtCo_yMn_z$, wherein $0.06 \leq y \leq 0.39$ and $0.04 \leq z \leq 0.33$.

7. The catalyst according to claim 1, wherein an absolute value of an adsorption energy in an adsorption site having a maximum oxygen atom adsorption energy is less than 1.0 eV.

8. The catalyst according to claim 1, wherein an absolute value of an adsorption energy in an adsorption site having a maximum oxygen molecule adsorption energy is less than 0.5 eV.

9. The catalyst according to claim 1, wherein an absolute value of an adsorption energy in an adsorption site having a maximum OH group adsorption energy is less than 2.3 eV.

10. The catalyst according to claim 1, wherein an absolute value of an adsorption energy in an adsorption site having a maximum water molecule adsorption energy is less than 0.19 eV.

11. The catalyst according to claim 1, wherein the catalyst particle is supported on a carbon fine powder carrier.

12. The catalyst according to claim 1 for use in a polymer electrolyte fuel cell, wherein a supporting density of the catalyst particles in the entire catalyst is 20 to 70% by mass.

13. The catalyst according to claim 2, wherein the PtCo alloy contained in the core is $PtCo_x$, wherein $0.14 \leq x \leq 0.33$.

* * * * *